(12) United States Patent
John et al.

(10) Patent No.: US 7,169,726 B2
(45) Date of Patent: Jan. 30, 2007

(54) CATALYST FOR ISOMERIZATION OF SOLID FISCHER-TROPSCH PARAFFINS AND METHOD FOR ITS PRODUCTION

(75) Inventors: Hans-Heino John, Halle (DE); Peter Birke, Langenbogen (DE); Rainer Schödel, Teutschenthal (DE)

(73) Assignee: KataLeuna GmbH Catalysts, Leuna (DE)

( * ) Notice: Subject to any disclaimer, the term of this patent is extended or adjusted under 35 U.S.C. 154(b) by 320 days.

(21) Appl. No.: 10/448,113

(22) Filed: May 30, 2003

(65) Prior Publication Data

US 2004/0092382 A1  May 13, 2004

(30) Foreign Application Priority Data

| May 31, 2002 | (WO) | .................... PCT/EP02/05970 |
| Aug. 13, 2002 | (DE) | ................. 102 37 651 |
| Dec. 2, 2002 | (DE) | ................. 102 56 404 |

(51) Int. Cl.
*B01J 29/06* (2006.01)
*B01J 29/068* (2006.01)

(52) U.S. Cl. ............... 502/64; 502/66; 502/74

(58) Field of Classification Search ................ 502/64, 502/66, 74
See application file for complete search history.

(56) References Cited

U.S. PATENT DOCUMENTS

| 4,518,485 | A |   | 5/1985  | LaPierre et al. |
| 4,612,108 | A |   | 9/1986  | Angevine et al. |
| 5,110,445 | A |   | 5/1992  | Chen et al. |
| 5,157,187 | A | * | 10/1992 | Le et al. ..................... 585/481 |
| 5,364,981 | A | * | 11/1994 | Knifton et al. ............. 568/698 |
| 5,494,870 | A | * | 2/1996  | Kukes et al. ................ 502/66 |
| 5,800,698 | A | * | 9/1998  | Tejada et al. ........... 208/216 R |
| 5,935,414 | A |   | 8/1999  | Sonnemans et al. |
| 6,017,840 | A | * | 1/2000  | Wu et al. ..................... 502/60 |
| 6,403,048 | B1 | * | 6/2002 | Kobayashi et al. ....... 423/245.3 |
| 6,413,898 | B1 | * | 7/2002 | Faber et al. ................. 502/64 |
| 6,652,735 | B2 | * | 11/2003 | Degnan et al. .............. 208/27 |
| 6,867,340 | B2 | * | 3/2005 | Oh et al. ................... 585/475 |
| 2002/0092797 | A1 | * | 7/2002 | Choi et al. ................ 208/134 |
| 2002/0117424 | A1 |   | 8/2002 | Drake et al. |

FOREIGN PATENT DOCUMENTS

| DE | 694 04 320 T2 |   | 1/1998 |
| DE | 692 21 327 T2 |   | 2/1998 |
| WO | WO 00/38834   | * | 7/2000 |

* cited by examiner

*Primary Examiner*—Elizabeth D. Wood
(74) *Attorney, Agent, or Firm*—Dickstein Shapiro LLP

(57) ABSTRACT

The present invention relates to a catalyst which consists of a combination of zeolite and platinum or palladium on aluminum oxide. The catalyst is suitable for converting solid Fischer-Tropsch paraffins into microcrystalline waxes.

29 Claims, No Drawings

CATALYST FOR ISOMERIZATION OF SOLID FISCHER-TROPSCH PARAFFINS AND METHOD FOR ITS PRODUCTION

FIELD OF THE INVENTION

The invention relates to a catalyst, and to a method for its production, which can be used for the hydroisomerization of a solid Fischer-Tropsch paraffin wax with numbers of carbon atoms between about 30 and 100.

BACKGROUND OF THE INVENTION

Wax mixtures or paraffin mixtures which can be used, for example, in the textile and packaging industries, in cosmetics, food technology or pharmaceuticals, frequently contain microcrystalline paraffins. Microcrystalline paraffins or waxes consist of mixtures of hydrocarbons which are solid at room temperature. Saturated hydrocarbons are concerned here, with a carbon chain length of about 25–100. Microcrystalline waxes, which contain isomeric paraffins as essential compounds, that is, branched paraffins (isoparaffins, i-paraffins) with a higher number of carbon atoms, are at present recovered from selected, high-molecular petroleum products (Ullmann's Encyclopedia of Industrial Chemistry, VCH Publishing Co., Weinheim 1996, Vol. A 28, 18–145). Microcrystalline paraffin recovered from petroleum contains, besides branched iso-alkanes, n-alkanes, naphthenes, and also aromatics.

Paraffins which according to the Fischer-Tropsch process are produced at high temperature from pure CO and $H_2$ synthesis gas in the presence of a catalyst, have on the contrary substantially normal-chain alkanes and only small proportions of branched alkanes, and are free from naphthenes, aromatics, and also from sulfur and oxygen compounds.

Theoretically, such Fischer-Tropsch paraffins, of the range of about 30–100 carbon atoms, are to be converted by isomerization into microcrystalline waxes. The main problem of the conversion of such long-chain paraffins into i-paraffins is the competing hydrocracking reaction. Since the known catalysts work at relatively high reaction temperatures, a large part of the paraffins is not only isomerized but also subsequently split to smaller fragments, which have to be separated as byproducts (A. B. R Weber: Hydroisomerization of paraffin wax, thesis, Excelsior Publishing Co., S'Gravenhage 1957). Corresponding proposed methods are therefore based on converting the Fischer-Tropsch product catalytically, with partial isomerization and partial cleavage, at temperatures at which liquid products arise, which are suitable for use as lubricating oils with high viscosity index.

From WO 01/74971, it is known to carefully isomerize a Fischer-Tropsch product with wide boiling range and also containing liquid products, and to recover a wax from the liquid hydroisomerizate by distilling off the lighter fractions. The hydrogenating temperature is given with a spread of 204–343° C. (however, example: 348° C.); the lower temperature range, not supported at all by examples, appears to be questionable as regards practicability. The high-boiling fractions of the raw material are blended with the wax recovered in this way. The catalyst is typically given as a cobalt-molybdenum catalyst on aluminosilicate. Zeolite Y or ultra-stable zeolite Y are given as suitable zeolites. It appears to be disadvantageous in this proposal that the additional process step of distillation has to be used, making the production of the soft microcrystalline wax more expensive.

The present methods of production of microcrystalline paraffins are not yet technically satisfactory. A catalyst is therefore desirable which can selectively convert the solid Fischer-Tropsch paraffin to microcrystalline paraffins in a single process step.

BRIEF SUMMARY OF THE INVENTION

The invention is therefore based on the technical problem of providing a catalyst, and a method of producing it, which overcomes the said disadvantages, and is in particular able to convert solid Fischer-Tropsch paraffins in a single process step, effectively and at favorable cost into microcrystalline waxes, that is, to isomerize the long-chain Fischer-Tropsch paraffins without reducing the number of carbon atoms of the molecules.

DETAILED DESCRIPTION OF THE INVENTION

The technical problem on which the invention is based is solved according to the invention by a catalyst which includes, and preferably consists of:

- 60–95 weight-% beta-type zeolite, relative to the combination of all components calcined at 800° C.;
- 5–39.8 weight-% of a large-surface gamma-aluminum oxide, calculated as $Al_2O_3$ and relative to the combination of all components calcined at 800° C.; and
- one or more metals of the eighth subgroup of the Periodic Table of the Elements, particularly platinum in amounts of 0.2–2.0 weight-%, with which aluminum oxide is combined, relative to the combination of all components calcined at 800° C.;

the one or more metals of the eighth subgroup of the Periodic Table of the Elements, particularly platinum, being combined with the aluminum oxide. This catalyst is particularly suitable for producing microcrystalline waxes, that is, paraffins from Fischer-Tropsch paraffins with number of carbon atoms of about 30–100. The paraffins produced have a high proportion of isoparaffins, in particular increased with respect to Fischer-Tropsch paraffins.

A preferred catalyst composition for the production of microcrystalline paraffins from Fischer-Tropsch paraffins, particularly with number of carbon atoms of about 30–100, includes:

- 75–90 weight-% beta-type zeolite, relative to the combination of all components calcined at 800° C.;
- 10–25 weight-% of a large-surface gamma-aluminum oxide, calculated as $Al_2O_3$ and relative to the combination of all components calcined at 800° C.; and
- one or more metals of the eighth subgroup of the Periodic Table of the Elements, particularly platinum particularly platinum in amounts of 0.4–1.0 weight-% relative to the combination of all components calcined at 800° C.;

the one or more metals of the eighth subgroup of the Periodic Table of the Elements, particularly platinum, being combined with the aluminum oxide. In an advantageous preferred embodiment of the present invention, the catalyst consists of these said components in the said weight ratios.

In connection with the present invention, the large-surface gamma-aluminum oxide has a specific surface of 150–300 $m^2/g$, relative to $\gamma$-$Al_2O_3$.

In connection with the present invention, "Fischer-Tropsch paraffins" is understood to mean solid alkanes which can in particular be recovered by means of the Fischer-Tropsch process, for example, from synthesis gas CO and $H_2$. These Fischer-Tropsch paraffins substantially have long-chain alkanes, unbranched and/or little branched; that is, they contain a high proportion of n-alkanes, for example, a ratio of iso- to n-alkanes of 1:5–1:11, with a carbon chain length of C20–C110, particularly C30–C100. The Fischer-Tropsch paraffins are practically free from aromatics, naphthenes, and oxygen compounds.

In connection with the present invention, the combination of all catalyst components calcined at 800° C. is free from water and ammonium.

In an advantageous, preferred embodiment of the invention, the catalyst is produced in that 60–95 weight-%, particularly 75–90 weight-%, relative to the combination of all components calcined at 800° C., is preferably beta-type zeolite in powder form (BEA-type according to W. M. Meier, H. H. Olson & Ch. Barlocher: Atlas of zeolite structure types, Fourth ed., Elsevier London, Boston, Singapore, Sydney, Toronto, Wellington, 1996):

with a $SiO_2$:$Al_2O_3$ molar ratio of 19.3:1 to 100:1; and
a residual alkali content of max. 0.05 weight-% (relative to zeolite calcined at 800° C.);

is mixed with 5–39.8 weight-%, particularly 10–25 weight %, relative to the combination of all components calcined at 800° C., of a gamma-aluminum oxide precursor, preferably in powder form, particularly an aluminum hydroxide, preferably boehmite or pseudoboehmite, the mixture is kneaded with addition of water and acid as peptization means, extruded, dried at temperatures of 80–200° C., preferably 100–200° C., and calcined at 400–600° C., and the moldings obtained are impregnated with a compound of one or more metals of the eighth subgroup of the Periodic Table of the Elements, particularly platinum, in which the noble metal is contained in anionic form, and subsequently thermally aftertreated in air, in particular dried and calcined, so that 0.2–2 weight-% of noble metal is contained relative to the combination of all components calcined at 800° C., and that the one or more metals of the eighth subgroup of the Periodic Table of the Elements, particularly platinum, is/are reduced to metal by means of a stream of hydrogen at elevated temperature.

Catalyst moldings are obtained in this manner which can be used in a heterogeneous process, the catalyst being preferably used as a fixed bed, and the liquefied wax being passed over it in trickle phase together with hydrogen at temperatures between preferably 200 and 270° C. In contrast to the catalysts known heretofore, this catalyst combination attains such a high activity for isomerization that a Fischer-Tropsch paraffin which is solid at normal ambient temperature can be used directly, and a microcrystalline wax is obtained in a single step. The properties of the microcrystalline wax can even be varied to a limited extent by a suitable choice of reaction parameters.

Beta-zeolite is a commercially available product. It is preferably used, according to the invention, as crystalline aluminosilicate powder with a composition of $Na_n(Al_nSi_{64-n}O_{128})$ with n<7. Instead of aluminum, boron or gallium can also occur isomorphically in the spatial silicate structure. Because of its high $SiO_2$ content, it can also be exposed to acid media without losing its crystalline structure; a portion of the aluminum tetrahedra being able to be removed from the crystal lattice. The beta-zeolite is preferably used as a fine powder with a particle size of in particular 0.5 µm to about 200 µm, measured with a laser particle size analyzer. The zeolite possesses pores with diameters of about 0.5 to about 0.8 nm. The structural 12-ring apertures have a width of 0.55 nm in the [001] direction and a width of 0.64, or respectively 0.76 nm in the [100] direction of the crystal lattice. Because of this extent of the apertures, the long, normal-chain paraffins are obviously able to enter at least partially into the internal structure of the zeolite with its acid centers.

So that the catalyst is particularly capable of isomerization, in a particularly preferred embodiment of the invention, alkali cations which are still present after synthesis can be exchanged for protons as quantitatively as possible. The exchange of alkali cations for protons is performed according to methods known per se, for example by exchange with water-soluble ammonium salts and subsequent calcination at 500° C. The introduction of protons can also be performed directly with dilute acids. After calcination, the zeolites are present in the Bronstedt or respectively Lewis acid form (acid centers), active for carbonium ion reactions.

In the present method of production of the catalyst according to the invention, in a preferred embodiment the zeolite is mixed, particularly as a powder, with a γ-aluminum oxide precursor, particularly aluminum hydroxide, preferably of boehmite or pseudoboehmite type. Boehmite consists of aluminum oxyhydroxide AlOOH, which simultaneously acts as a binder for the zeolite and a support for a hydrogenating metal component, or contains these in substantial proportions. Both powders are mixed together and simultaneously or thereafter, dilute acid, for example mineral acid, preferably nitric acid, or organic acid, such as formic acid or acetic acid, is added as a peptizing agent, together with an amount of water such that a moldable, plasticized mass arises with intensive working of the mass by kneading. To increase the plasticity, plasticizing agents, in particular water-soluble cellulose ethers, are added in small amounts up to about 5 weight-% relative to the powder substances. This mass is extruded, for example by means of a screw extruder through nozzles, so that moldings arise in strand form with a selectable diameter and profile. The extrudates, possibly broken to a given length, are then dried at temperatures of 80° C. to 200° C., particularly 100° C. to 200° C., and in a further step are heat treated at temperatures of 400–600° C., in particular calcined, so that all or substantially all organic fractions, water, and nitrate or ammonium ions which possibly may be present, escape from the moldings.

On calcination at temperatures above about 350° C., the aluminum oxide precursor transforms into gamma-aluminum oxide, which has a specific surface of 150–350 $m^2/g$, relative to $Al_2O_3$, and a pore volume of 0.3 to about 1.0 $cm^3/g$, relative to $Al_2O_3$. The pores of the aluminum oxide preferably have a diameter of 3–50 nm, due to which the aluminum oxide is capable of taking up large molecules and transporting them to the zeolite crystals.

The calcined moldings are impregnated with a solution which contains compounds of the metal(s) of the eighth subgroup of the Periodic Table of the Elements, particularly the platinum. For this, $H_2[PtCl_6]$ and $H_2[PdCl_4]$ are particularly suitable. However, other suitable compounds which contain the noble metal in anionic form can be used. In a preferred embodiment, the noble metal compounds are advantageously used in aqueous solution. Advantageously and in a preferred embodiment of the invention, the concentration of the noble metal in the solution is adjusted so that its final concentration in the catalyst after the solution is taken up is adjusted according to single pore filling of the moldings with the solution.

After impregnation of the moldings with the solution of the compounds containing noble metal, the moldings, in a preferred embodiment of the invention, are dried in a device in order to remove water. The moldings are then calcined, advantageously and in a preferred embodiment, in a dry air stream, the volatile compounds which become free being carried away in the exhaust gas. If necessary, nitrous gases which arise are to be destroyed.

The noble metals are present after this, finely distributed as metal oxy-compounds, in particular platinum oxy-compounds, combined with the large-surface aluminum oxide, while the zeolite crystals themselves contain no hydrogenating metal components. Before being put to use, the catalyst is reduced in a hydrogen-containing gas stream, in particular heated to temperatures of 100–480° C., in order to deposit the noble metal in finely-divided form on the aluminum oxide. The metal agglomerates are thereafter present, advantageously and in a preferred embodiment of the invention, in such a form that at least 30% and at most 70% of all metal atoms are capable of adsorption of a CO molecule.

The metal components function as portions of the catalyst which are capable of hydrogenation and are able to activate the long-chain paraffins to carbonium ions. The latter react at the acid centers in the catalyst, with displacement of $CH_3$ groups on the long chains. Single methyl group branched paraffins emerge from the pore openings after conversion primarily in the 2-, 3-, 4- and/or 5-position on the carbon chain.

The catalyst according to the invention can be used, for example, in the form of extrusions, cylinders, granulates, pellets, tablets or powder.

In a preferred embodiment of the present invention, the catalyst can be used in the presence of hydrogen at an $H_2$ partial pressure of 5–180 bar.

In a preferred embodiment of the present invention, the catalyst can be used at a $H_2$: feed ratio of 100:1 to 2,000:1 $Nm^3/m^3$.

In a preferred embodiment of the present invention, the catalyst can be used at a loading of 0.1–1 feed volumes/ catalyst volume per hour.

In a preferred embodiment of the present invention, the catalyst can be used at a temperature of 200–270° C.

The catalyst, in a preferred embodiment of the present invention, can be used in the form of small particles suspended in the feed at temperatures of preferably 200–270° C. and elevated pressure in the presence of hydrogen, in order to convert Fischer-Tropsch paraffin into microcrystalline wax. Light fractions which possibly arise can be distilled off by hydrogen distillation (stripping).

In a preferred embodiment of the present invention, the catalyst is advantageously built into a reactor as a fixed bed, through which the feed is allowed to flow slowly together with hydrogen at temperatures of preferably 200–270° C. The catalyst according to the invention can be used in a continuous, semi-continuous, or discontinuous type of process.

The obtained singly isomerized compounds have the character of microcrystalline waxes and are used for very varied applications (cf. Ullmann's Encyclopedia of Industrial Chemistry, VCH Publishing Co., Weinheim 1996, Vol. A 28, 18–145). The degree of isomerization, and thus the properties of the microcrystalline wax, can be adjusted to a certain extent in dependence on the reaction conditions, without a distillation or a subsequent blending being required.

Further advantageous embodiments will become apparent from the dependent claims.

The invention will be described in detail using the following example.

EXAMPLE

Production of a Catalyst 300 g of commercially available beta-zeolite with a $SiO_2:Al_2O_3$ molar ratio of 23.3 in the metal cation free form (alkali content less than 0.05 weight-% relative to zeolite calcined at 800° C.), as a powder with a particle size of 0.5 to about 50 μm, 62.8 g of commercially available aluminum oxide hydroxide as a fine powder, and 8.4 g of water-soluble cellulose ether, are intensively mixed together. Then 30 ml of diluted nitric acid with 128 g $HNO_3/l$ and 350 ml of deionized water are added and intensively kneaded for an hour. A moldable, kneadable mass results. The mass thus obtained is pressed with an screw extrusion press through nozzles with cylindrical apertures of 1.5 mm diameter, so that strands of extrudates arise. These are dried for six hours in a drying oven at 120° C.

The moldings are broken to a length of 3–5 mm and are calcined for three hours at 550° C. in a thin layer on a metal sheet in an electric muffle furnace. Solid moldings are obtained with a bulk density of 400 g/l.

The removable amount of water of the moldings is determined at room temperature, and corresponds to the pore volume (=110% relative to the catalyst weight). A solution of 1.636 g $H_2PtCl_6$ in 242 ml water is sprayed onto 220 g of the moldings while they are moved. After a time of 10 minutes for action, the moldings are dried while being moved, until the main quantity of liquid has evaporated and the moldings no longer cling together. After this, the impregnated moldings are dried at 120° C. in a drying oven. The dried moldings are heated at 100° C./h to 450° C. in a stream of dry air in a vertical oven, and are kept at 450° C. for an hour.

The moldings are then cooled in the oven to ambient temperature; the air stream is replaced with pure nitrogen, until the oxygen content of the outflowing gas is under 0.5 vol.-%, and then changed over from nitrogen to hydrogen. The oven is again heated up at 100° C./h to 450° C., and the catalyst is treated, that is, reduced, in flowing hydrogen for three hours at this temperature. The catalyst is then allowed to cool in the stream of nitrogen and can be removed. The obtained catalyst A is stable in air. The platinum content is 0.8 weight-% relative to the combination of all components calcined at 800° C.

Catalytic Test

The above-described catalyst A was comminuted to a particle size of 160–315 μm, and 4 g of this comminuted catalyst was stirred into 180 g of a Fischer-Tropsch paraffin ("feed") at a temperature of 120° C. The mixture was filled into an autoclave. After closing the autoclave, a hydrogen pressure of 50 bar was built up and the mixture was heated to 250° C. with stirring and further treated for seven hours, with stirring. The autoclave was thereafter cooled again to 120° C., the product was removed from the autoclave, and the catalyst was separated and investigated. The product characteristics were compared with those of the feed (see Table).

TABLE

Characteristics of the Feed and of the Hydroisomerizate

|  | Feed | Hydroisomerizate |
|---|---|---|
| Number of C atoms (>90%) | 30–100 | 25–100 |
| Solidification point, ° C. = congealing point | 97 | 86.5 |
| Enthalpy of melting, ΔH | >200 | 127 |
| Penetration at 25° C. | 1–2 | 42 |
| Viscosity at 120° C., cs | ~12 | 15.4 |
| Isoalkane wt % | ~12 | 47 |
| <C 22 in wt. % | 0 | 2–3 |

The hydroisomerizate clearly shows different properties, which correspond to a microcrystalline wax, from the starting material. The proportion of i-paraffins is considerably increased with respect to the feed.

Comparison Example

Two comparison catalysts B and C were produced and the same catalytic test as described above was performed.

Production of Catalyst B 200 g of the same zeolite powder as in the example according to the invention were exchanged with Pt(NH$_3$)$_4$Cl$_2$ solution. Thereafter the platinum content was 0.8 weight-% in relation to the water- and ammonia-free composition. The powder was dried at 120° C., pressed into tablets 5×5 mm, calcined at 550° C. in an air stream analogously to the example according to the invention, and likewise reduced with hydrogen at 450° C. analogously to the example according to the invention.

Production of Catalyst C 20 g of an aluminosilicate, amorphous to X-rays, with a Si/Al (atomic) ratio of 13.5, a specific surface of 630 m$^2$/g and a pore diameter of 4 nm, was mixed with 5 g of boehmite powder, with the addition of 0.30 g HNO$_3$ and 700 mg of water-soluble cellulose ether and also enough water to give a kneadable mass, which was pressed through a jet having an aperture of 1.5 mm. The extrudates obtained were dried at 120° C. and calcined at 550° C. The calcined moldings were impregnated, in the same way as already described in the example according to the invention, with a solution of H$_2$PtCl$_6$, dried, and calcined at 450° C., and also reduced with hydrogen in a stream of dry hydrogen at 450° C.

Both catalysts were comminuted to a particle size of 160–315 μm and catalytically tested under the same conditions as in the example according to the invention. An i-alkane content of 40% was determined for catalyst B, and an i-alkane content of 10% for catalyst C.

It is apparent from the investigation results that the composition and manner of production of the catalyst according to the invention are particularly suitable for solving the problem according to the invention. In particular, a particularly high activity was obtained in the desired isomerization.

The invention claimed is:

1. Catalyst for the production of microcrystalline waxes from Fischer-Tropsch paraffins, consisting of 60–95 weight-% zeolite of beta type, relative to the combination of all components free from water and ammonium, 5–39.8 weight-% of gamma aluminum oxide having a specific surface area of 150–350 m$^2$/g, calculated as Al$_2$O$_3$ and relative to the combination of all components free from water and ammonium, and platinum and palladium or palladium in an amount of 0.2–2.0 weight-%, relative to the combination of all components free from water and ammonium, the platinum and palladium or palladium being combined with the gamma-aluminum oxide and not with the zeolite.

2. Catalyst according to claim 1, containing 75–90 weight-% beta-type zeolite, 10–25 weight-% of gamma-aluminum oxide, and platinum in an amount of 0.4–1.0 weight-%.

3. Catalyst according to claim 1, wherein the zeolite has a SiO$_2$:Al$_2$O$_3$ molar ratio of 19.3:1–100:1.

4. Catalyst according to claim 1, wherein the zeolite has a residual alkali content of at most 0.05 weight-% relative to the zeolite free from water and ammonium.

5. Method of production of a catalyst according to claim 1, wherein a beta-type zeolite is mixed with a gamma aluminum oxide precursor, kneaded, extruded, dried, and calcined, and the moldings are impregnated with a compound of platinum and palladium or palladium and are then thermally after-treated in a dry air stream so that 0.2–2 weight-% of the platinum and palladium or palladium is/are contained, relative to the combination of all components free from water and ammonium, wherein the compound of platinum is H$_2$PtCl$_6$ and the compound of palladium is H$_2$PdCl$_4$ or H$_2$PdCl$_6$.

6. Method according to claim 5, wherein the zeolite or aluminum oxide precursor or both are used in the form of powder.

7. Method according to claim 6, wherein the powder-form beta-type zeolite has a SiO$_2$:Al$_2$O$_3$ molar ratio of 19.3:1–100:1.

8. Method according to one of claims 6 and 7, wherein the powder-form beta-type zeolite has a residual alkali content of at most 0.05 weight-%, relative to the combination of all components free from water and ammonium.

9. Method according to claim 6, wherein the powder-form beta-type zeolite is used in an amount of 60–95 weight-%, relative to the combination of all components calcined at 800° C.

10. Method according to claim 5, wherein the gamma-aluminum oxide precursor is used as boehmite or pseudo-boehmite.

11. Method according to claim 6, wherein the powder-form gamma-aluminum oxide precursor is used in an amount of 5–39.8 weight-% relative to the combination of all components free from water and ammonium.

12. Method according to claim 5, wherein the mixture of gamma aluminum oxide precursor and zeolite is kneaded with the addition of water and acid as peptizing agent.

13. Method according to claim 5, wherein the γ-aluminum oxide precursor and the zeolite are mixed or kneaded with the addition of a plasticizing agent.

14. Method according to claim 5, wherein the drying takes place at temperatures of 80° C.–200° C.

15. Method according to claim 5, wherein the dried moldings are calcined at temperatures of 400° C.–600° C.

16. Method according to claim 5, wherein the impregnated catalyst is subsequently reduced with hydrogen.

17. Catalyst according to claim 1, containing 75–90 weight-% beta-type zeolite, and 10–25 weight-% of gamma-aluminum oxide.

18. Catalyst according to claim 17, containing palladium in the absence of platinum.

19. Catalyst according to claim 18, wherein the zeolite has a residual alkali content of at most 0.05 weight-% relative to the zeolite free from water and ammonium.

20. Catalyst according to claim 19, wherein the zeolite has a $SiO_2:Al_2O_3$ molar ratio of 19.3:1–100:1.

21. Catalyst according to claim 17, containing palladium and platinum, in which the platinum is an amount of 0.4–1.0 weight-%.

22. Catalyst according to claim 21, wherein the zeolite has a residual alkali content of at most 0.05 weight-% relative to the zeolite free from water and ammonium.

23. Catalyst according to claim 22, wherein the zeolite has a $SiO_2:Al_2O_3$ molar ratio of 19.3:1–100:1.

24. Catalyst according to claim 17, wherein the zeolite has a $SiO_2:Al_2O_3$ molar ratio of 19.3:1–100:1.

25. A catalyst for the production of microcrystalline waxes from Fischer-Tropsch paraffins which is made by the method of claim 5.

26. A catalyst for the production of microcrystalline waxes from Fischer-Tropsch paraffins which is made by the method of claim 8.

27. A catalyst for the production of microcrystalline waxes from Fischer-Tropsch paraffins which is made by the method of claim 9.

28. A catalyst for the production of microcrystalline waxes from Fischer-Tropsch paraffins which is made by the method of claim 14.

29. A catalyst for the production of microcrystalline waxes from Fischer-Tropsch paraffins which is made by the method of claim 16.

* * * * *